United States Patent [19]

Attström et al.

[11] Patent Number: 5,260,282
[45] Date of Patent: Nov. 9, 1993

[54] SALIVA SUBSTITUTE

[75] Inventors: Rolf Attström, Malmö; Per O. Glantz; Håkan Håkansson, both of Lund; Kåre Larsson, Bjärred, all of Sweden

[73] Assignee: Camurus AB, Malmö, Sweden

[21] Appl. No.: 864,395

[22] Filed: Apr. 6, 1992

[30] Foreign Application Priority Data

Apr. 10, 1991 [SE] Sweden ............................. 9101076-9

[51] Int. Cl.⁵ .......................................... A61K 31/715
[52] U.S. Cl. ..................................................... 514/54
[58] Field of Search .......................................... 514/54

[56] References Cited

FOREIGN PATENT DOCUMENTS 676130 5/1939 Fed. Rep. of Germany .
2557797 7/1985 France .
546589 7/1942 United Kingdom .

OTHER PUBLICATIONS

"Unconventional Sources for Food and Feed-Studies on Linseed Mucilage and Fish Silage" (1990) by Kirstin Wannerberger from Food Technology series, the University of Lund.

"Rheological and Chemical Properties of Mucilage in Different Varieties from Linseed" (*Linum usitatissimum*) by K. Wannerberger, T. Nylander and M. Nyman, Manuscript for publication.

"Fish Silage-Influence of Ensiling Conditions on Fat Oxidation" by K. Wannerberger and B. Sivak, Manuscript for publication in Int. J. Food Sci. Technol.

"A double-blind crossover trial of CMC-and mucin--containing saliva substitutes", by L. L. Visch et al., Int. J. Oral Maxillofac. Surg., vol. 15, pp. 395 to 400 (1986).

"Vlastnosti l'Anovécho Mucínu. VII.*) Charakteristika niektorych z purifikovaného produktu", vol. 19, No. 4, pp. 143 to 146 (1970).

"Functional Role of Linseed (linum usitatissimum L.) Polysaccharide in Steamed Pudding (idli)", by N. S. Susheelamma, J. Fd. Sci. Technol., vol. 26, No. 1, pp. 16 to 20 (1989).

"Rheological and Chemical Properties of Mucilage in Different Varieties from Linseed (Linum usitatissimum)", by K. Wannerberger et al, Acta Agr. Scand., vol. 41, pp. 311 to 319 (1991).

*Primary Examiner*—John W. Rollins
*Attorney, Agent, or Firm*—Burns, Doane, Swecker & Mathis

[57] ABSTRACT

A saliva substitute, the characteristic feature of which is that it comprises water-soluble linseed polysaccharides. Said substitute is preferably in the form of an aqueous solution having a viscosity within the range of 1-30 mPa.s, most preferably 2-10 mPa.s. The substitute can be prepared by extracting the polysaccharides from linseed by means of water or a water solution containing inorganic salts. In addition to the fact that said substitute is useful as a saliva substitute it can also be utilized as a carrier for pharmaceuticals adapted for oral applications.

25 Claims, No Drawings

SALIVA SUBSTITUTE

TECHNICAL FIELD

The present invention relates to the field of saliva substitutes. More specifically it has been shown that a certain type of polysaccharides possess such properties that they can work as saliva substitutes for individuals with developed reduced salivary secretion. Thus, the invention relates to a novel saliva substitute, to a process for the preparation thereof, and to a specific use of the same as a carrier or vehicle in connection with pharmaceuticals.

BACKGROUND OF THE INVENTION

A reduced salivary secretion arises or develops with increasing age. Thus, most elderly people have problems with a dry mouth. Some general diseases also give rise to a reduced secretion of saliva, so called hyposalivation. The most prominent one thereof is Sjoegren's syndrom. Furthermore, several generally used medicins, inter alia antihypertensives, antiulcer agents and antipsychotics, cause such a hyposalivation. In other words dryness of the mouth, or xerostomia, is a common disease that affects a large number of the population transiently or permanently.

The reduced secretion of saliva causes subjective symptoms in the form of burning tongue, mouth, pharynx and esophagus and sensitivity to spicy food and beverages. Some individuals are also affected as to speech and swallowing. Objectively dryness of the mouth often causes caries and periodontitis, which are difficult to treat since the reduced secretion of saliva results in a more pronounced retention of bacteria in the oral cavity and on the teeth. The resistance of the mucosa against colonization of bacteria is reduced and especially fungal infections are common in connection with individuals with xerostomia. Furthermore, people carrying so called plate prosthesis often have great problems with the retention of the prosthesis as well as infection of the mucosa as consequences of the dryness of the mouth.

There are agents against xerostomia on the market, but these are very varying as to efficiencies. Serious shortcomings in connection with the agents on the market are inter alia short and minor effects and in some cases a disagreeable taste results. Moreover, in general the prices are high which means an economic drawback for persons which have to utilize such agents continuously.

The salivary glands of the mouth normally produce around 1-1.5 l of saliva per 24 hours, and it must be considered unrealistic to utilize a saliva substitute which has to be taken in such a volume per 24 hours. Therefore, said agent has to possess such retention properties that it is retained and lubricates the teeth and mucosas for a relatively long time after a dosage has been taken. Furthermore, the preparation has to be swallowable so as to reduce the problems or symptoms in the pharynx and the esophagus.

According to the present invention novel saliva substitutes are provided which eliminate or at least significantly reduce the disadvantages of the previously known agents and which fulfil the requirements for agents of this type.

GENERAL DISCLOSURE OF THE INVENTION

According to the present invention it has been shown that a specific group or type of polysaccharides work extremely well as a saliva substitute. This is unexpected since different starch and cellulose derivatives have been studied in these connections and since it has then been found that especially the extremely good lubricating and dispersing properties of the saliva have not been obtainable with a practically useful saliva substitute as a consequence thereof.

More specifically the present invention is based on the discovery that polysaccharides of the types which are present in linseed possess a very unusual combination of rheological and surface-chemical properties, which make them extremely suitable for the application defined above. That is, the present invention relates to a saliva substitute, the characteristic feature of which is that it comprises water-soluble linseed polysaccharides.

In other words those polysaccharides which are intended to be used as the main ingredient of the saliva substitute according to the invention are of the type that is obtainable by a simple extraction in water of said polysaccharides directly from linseed. One way of obtaining said polysaccharides, which will be described more in detail below, therefore is to directly dissolve the polysaccharides from linseed by means of water, but of course the invention is not limited to such an embodiment. Any polysaccharide fraction having the corresponding or essentially similar composition and obtainable in any other way, even synthetically, is thus within the scope of the invention, as a corresponding effect should be obtainable thereby. This can for instance mean that one can extract the same polysaccharides, or the major proportion thereof, from linseed by means of water in combination with other solvents, e.g. ethanol (for instance up to 70% of ethanol in water) or even completely other solvents than water, provided that said combinations or other solvents dissolve essentially the same polysaccharides as water. However, a disadvantage of such an extraction is that it will then be necessary to evaporate or strip the "extra" solvent(s) utilized and then optionally redissolve the extract in water before it can be used as a saliva substitute, provided the used solvent is not directly physiologically acceptable.

The "water-soluble linseed polysaccharides" according to the invention may be obtained by a simple dissolution or extraction from linseed in water of approximately room temperature. However, the invention is not limited to said water temperature, as a dissolution at a lower or higher temperature should give similar results. Thus, the experiments made seem to indicate that the exact composition of the polysaccharide fraction is not especially critical. Thus, merely in Sweden there are some tens of linseed varieties, and all those varieties should be useful according to the invention. On the contrary there can be great variations as to the viscosity between the different varieties or types, and rather it has been shown that the viscosity has a greater influence upon the properties of the polysaccharide fraction as said saliva substitute.

A preferable saliva substitute according to the present invention is therefore characterized in that it is present in the form of an aqueous solution of the above-mentioned linseed polysaccharides, which solution has a viscosity within the range of 1-30 mPa.s (cP), it of course being understood that said aqueous solution is physiologically acceptable.

In this context it should be noted that in the present case the viscosity has been determined by a measurement in a Bohlin VOR-rheometer in the conventional way (sheer rate 10 s$^{-1}$)

A preferable viscosity range is 1–20 mPa.s, the range of 2–10 mPa.s being especially preferable.

Thus, it is remarkable with the great variations as to viscosities between solutions of polysaccharides from different varieties of linseed. More specifically it has been shown that one percent by weight of the polysaccharide fraction in water may vary as to viscosity within the range of from about 0.02 to about 0.28 Pas. In those cases where the utilized linseed variety does not give any viscosity within the desired range at a water extraction, an adjustment of said viscosity may be made merely by an adjustment of the concentration of the linseed polysaccharides in the aqueous solution. This should mean that all linseed varieties are useful as starting materials for the saliva substitute according to the invention.

It can also be added that it has been shown that high relative proportions of xylose in the polysaccharides give a high viscosity, which should be utilizable in for instance a genetic processing or engineering towards an ideal composition for a saliva substitute.

In connection with the above-mentioned expression "aqueous" solution it should be noted that a pure water solution of the linseed polysaccharides is not necessarily referred to. Any aqueous liquid or solution which is acceptable to the human body should be useful, which inter alia may mean water containing such inorganic salts which are present in common saliva. Sodium chloride and potassium bicarbonate can be mentioned as examples thereof. The concentrations of said salts may then preferably be up to those concentrations which are present in natural or common saliva. The total contents of salts in common saliva is of the order of magnitude of 3 mg per ml of water (saliva), which should thus represent a preferable upper limit as to the total salts content. However, theoretically it might be possible to use an even higher concentration of salts, but generally such a solution would be perceived as having a too salty taste.

As concerns the viscosity properties of linseed polysaccharides of the type which are useful according to the present invention reference is made to K. Wannerberger (1990) Unconventional Sources for Food and Feed, Food Technology Series, the University of Lund, S-221 00 Lund.

From the above-mentioned it can be gathered that a preferable embodiment of the saliva substitute according to the invention is a substitute wherein the linseed polysaccharides have been obtained by an extraction from linseed with water or a salt solution of the type referred to above.

Preferably the above-mentioned extraction is performed at a temperature around room temperature.

According to another preferable embodiment of the saliva substitute according to the invention the aqueous solution additionally contains one or more flavoring agents to have a more pleasant taste and/or to mask some salty taste. One preferable flavoring agent is xylitol. Another example of a flavoring agent is a fruit juice, e.g. lemon juice. Furthermore, it can suitably contain a conventional preservative.

According to still another preferable embodiment of the saliva substitute the aqueous solution contains one or more therapeutically active agents, such as agents against fungal, viral and/or bacterial diseases, to have a concurrent treatment against such diseases. A preferable additive is cortico steroids, which are useful for instance against inflammatory mouth sores. Other preferable additives may be xylitol and fluorine compounds (both being favorable to the teeth as is known per se). Sodium fluoride is one example of a fluoride for such a use. Said fluorine compounds can generally be used in amounts of 0.5–1.5, preferably 0.8–1.2 mg/liter.

The preparation of the saliva substitute according to the present invention has been discussed to some extent above. In this context the invention relates to a process wherein linseed in contacted with water, which optionally contains the desired additives, e.g. inorganic salts and/or flavoring agents, so as to extract polysaccharides from said linseed and separating the aqueous phase containing dissolved polysaccharides from the solid linseed residue.

According to one embodiment the obtained aqueous phase can then be dried, e.g. by lyophilization, to a dry product which is then dissolved in water to be used as the saliva substitute. Another embodiment means that the obtained aqueous phase is used directly as said saliva substitute, provided that it has the desired viscosity. If this is not the case, the viscosity can be adjusted by simply adjusting the concentration of the polysaccharide fraction in the aqueous liquid.

If the desired additives were not present from the beginning, such additives can of course be added at a later stage of the process.

If required, also a sterilization of the solution referred to is performed, which is applicable to both of the above-mentioned alternatives or embodiments. Such a sterilization is performed in a manner known per se, for instance by heating, such as to about 100° C., with a maintenance time of some minutes and then preferably rapid cooling.

As additional practical details in connection with the process the following can be mentioned.

The proportions or the ratio between liquid (water) and linseed in the extraction is preferably selected, as was previously mentioned, in such a way that the obtained solution containing the dissolved polysaccharides has the desired viscosity per se. Typically this means about 50–150 g, e.g. 100 g, of linseed per liter of liquid.

In addition thereto, in order to optimize the yield of the extraction, one should work with a thin layer of linseed and a similarly relatively thin layer of liquid.

The extraction is typically performed for at least about 3–4 hours.

Furthermore, it should of course also be checked that the seeds do not contain any mold which may contain toxins (inter alia allergenic toxins) and preferably the seeds should be rinsed rapidly in order to remove dust, gravel, etc.

Generally it can also be said that the used linseed does not have to be milled or crushed before the extraction. This means that the residual seeds can be utilized at a linseed extraction.

As concerns the process according to the present invention it can be added that those features which have been disclosed in connection with the agent or substitute per se are also applicable to said process, i.e. as concerns especially preferable embodiments of the invention.

As to the process claimed it can generally be said that the yield of the polysaccharide fraction is typically of the order of 4 percent by weight (dry weight of polysaccharides) based on the solids content of the linseed. After the drying operation the fraction is essentially lipid free (generally below 1%) and the protein contents thereof is generally lower than 10% (typically 2-9% according to the Kjeldahl analysis).

Another aspect of the invention relates to an aqueous solution having the above-mentioned characteristics and for use as a saliva substitute.

The saliva substitute according to the invention can be utilized in two ways. Firstly it can of course be utilized merely for rinsing the oral cavity, whereupon it is spitted out again. Thanks to its content of pure natural products and its pleasant taste it may, however, also well be swallowed, the effect thereof being not only a lubricating effect in the mouth and in the pharynx but also an effect throughout the whole gastro intestinal tract.

In other words the substitute according to the present invention has a taste of its own which is accepted by man, but of course it is possible, if desired, to add flavoring agents as well as other additives of conventional types. Although the linseed polysaccharides represent the major constituent of the active ingredient of the saliva substitute, it is also possible to add minor amounts of other previously known saliva substitutes without deviating from the general idea of the present invention.

One interesting aspect of the present invention is, however, represented by the case where the saliva substitute is also utilized as a carrier for pharmaceuticals intended to be taken orally. However, this use is not limited to some specific pharmaceutical(s) but works for different types of pharmaceuticals intended to be taken orally and with which the present polysaccharides are compatible. Examples of interesting pharmaceuticals in this context are, however, analgestics or antibiotics as well as the previously mentioned cortico steroids. In addition to the fact that this means a preferable and pleasant way of swallowing said pharceutical it is also interesting with reference to an even more continuous distribution of addition of the pharmaceutical with time, i.e. throughout the day and night.

Therefore, in summary, still another aspect of the invention relates to the use of a saliva substitute according to the above-mentioned definitions as a carrier for pharmaceuticals for oral applications.

EXAMPLES

The invention will now be further described by the following, non-limiting examples relating to the manufacture and use of the saliva substitute according to the invention.

EXAMPLE 1

Linseed in an amount of 100 g and of the variety Szegedi 62 was added to 1 liter of distilled water and the mixture was mixed throughout 24 hours. The obtained solution was separated from said linseed by centrifugation and was lyophilized.

When used as a saliva substitute the lyophilized product is then stirred into ordinary tap water (of a good quality). A concentration of one percent by weight thereof then gives a viscosity of 280 mPa.s and by a dilution thereof to a concentration of 0.2 percent by weight it works very well as a saliva substitute.

EXAMPLE 2

To a water solution containing 1.3 mg/ml of sodium chloride and 1.7 mg/ml of potassium bicarbonate linseed of the variety Regina was added in a weight ratio solution:seed of 20:1. The solution was stirred carefully for about 12 hours, whereupon the linseed portion was separated by filtration. The solution was sterilized by heating to 100° C. and a maintenance time of 10 minutes, whereafter it was aseptically packed.

This solution, the viscosity of which was 210 mPa.s, was shown to be useful as a saliva substitute after a tenfold dilution thereof.

EXAMPLE 3

1 liter of a water solution consisting of 0.1% (w/w) of sodium chloride, 0.03% of disodium hydrogen phosphate and 0.02% of calcium chloride (anhydrous) was prepared. 100 g of linseed, variety Tadorna, was extracted in this water solution for 10 hours by slow stirring at room temperature. The seeds were then separated by filtering. In order to obtain an antimicrobial protection, lysozyme (which is a natural antimicrobial agent in saliva) was added just to the point where the clear solution starts to become opalescent. It is hard to give an exact concentration for this as it is strongly dependant on the type and batch of lysozyme used, but the aim is to obtain maximum concentration at this ionic strength. The final solution was freeze-dried and packed.

EXAMPLE 4

The same water solution as in example 3 was prepared and 1 p.p.m. of sodium fluoride was added, in order to strengthen the teeth minerals by exchanging the hydroxyl group against fluoride in the apatite. To 1 liter of this solution 100 g of Tadorna linseed were added and the extraction and seed separation were done as in example 3. The final solution was heated to 130° C. for five seconds and aseptically packed into 2 ml plastic pipettes (using industrial standard equipment for aseptic processing).

EXAMPLE 5

The composition below, from Tadorna linseed, was evaluated as a saliva substitute on a number of patients in the following way.

PREPARATION OF TADORNA LINSEED 6 kg of linseeds were washed with 2×10 liters of UF water which was then screened off. The seeds were charged into an extraction tank and 40 liters of UF water were added. The mixture was stirred for 16 hours. The stirring was stopped and the seeds were allowed to settle. The seeds were separated by filtration with a nylon mesh.

1 g of sodium benzoate/liter was added.

The viscosity was measured to about 30-40 mPa.s.

The product was filled on bottles and autoclaved at 100° C. for 2 minutes.

The viscosity was measured to 22 mPa.s and the pH was 5.5.

AGENTS AND METHOD

Seven patients, 39-60 years of age, with xerostomia were recruited. The diagnosis for some of the patients was Sjoegren's syndrom. The patients answered questions relating to xerostomia before and after seven days of use of the composition according to Example 2. Patients 1 and 5 utilized a solution from one batch and the other patients a solution from another batch of the composition.

In the results presented there are given numeral ratings of the verbal alternatives of the inquiry. The verbal alternatives and the corresponding ratings are given below. An increasing rating was selected for the xerostomia as well as for the effect of the composition. Thus, the rating 5 means very potent symptoms and very much less potent symptoms, respectively, after use of the tested agent.

| Verbal alternative | Rating |
|---|---|
| XEROSTOMIA | |
| Very much potent | 5 |
| Much potent | 4 |
| Rather potent | 3 |
| Some symptoms | 2 |
| Minor symptoms | 1 |
| EVALUATION OF THE EFFECT OF THE COMPOSITION | |
| Very much less | 5 |
| Much less | 4 |
| Relatively much less | 3 |
| Less to some extent | 2 |
| A little less/not less | 1 |

The effects upon the oral hygiene condition and the gingivitis were registered by determinations of the plaque index and the gingival index before and after 7 days of use of the composition.

RESULTS

General feeling of dryness of the mouth

The patients had been troubled with symptoms of dryness of the mouth for periods varying between 3 and 20 years. The majority of said patients had been troubled thereby for about 5-7 years. The feeling of dryness of the mouth was evaluated as very much potent to rather potent and most of the patients stated that their symptoms had been very potent. During 7 days of use of the composition the symptoms of dryness of the mouth were reduced for all tested persons. Most of them stated that the dryness of the mouth had been relatively much less to very much less during the test period. Only one of the persons stated that the effect of the composition had been minor (tables 1 and 2).

Burning Mouth, Pharynx and Esophagus

The analysis of the burning mouth as a consequence of dryness of the mouth was divided into anatomic regions: cheeks, tongue, lips, pharynx and esophagus. The patients felt that dryness of the mouth caused great problems as to burnings, especially burning tongue, pharynx and esophagus. The use of the composition imparted to most of the patients very much less to much less symptoms. The tested persons with the most potent symptoms generally stated the best effects of the composition (tables 3, 4, 5, 6 and 7).

Taste, Speech and Chewing

Most of the patients stated that taste, speech, swallowing and chewing were negatively influenced by the dryness of the mouth. The gradations of the responses of the patients indicate that the symptoms were pronounced and very much troubling. The composition had a good to very good effect on the functions of speech and swallowing, while the effect was somewhat less as to taste and chewing (tables 7, 8, 9, 10 and 11).

Oral Hygiene and Oral Mucosa

Some of the patients were troubled by fissures of the oral mucosa and had problems with brushing their teeth. The composition had some positive effect also upon said symptoms. Three of the patients stated that they had a bad taste in their mouth which was very embarrassing. The other persons had minor problems with bad taste in their mouths. The composition reduced this symptom for 6 of the tested persons (tables 12, 13 and 15).

Plaque and Gingivitis

The registrations of the plaque index and the gingival index before and after 7 days of use of the composition indicate that the oral hygiene level was somewhat better after the test period. The average index value decreased from 45 % of the tooth surfaces with bacteria deposits before to 23% after the use of the composition. For the gingival index, i.e. gingivitis, the corresponding values were 18% and 14%, respectively, (table 16).

Comments From the Patients

Problems with mouth functions, such as speech, taste and swallowing, were referred to. Furthermore, there were complaints as to problems in the upper respiratory tracts. The neutral taste and the consistency of the composition were experienced as pleasant. A few persons stated that the solution had some minor taste of salt and caused some minor nausea. It was a great advantage that the solution could be swallowed as it could thereby alleviate the symptoms of the pharynx and esophagus. The preparation in the form of a solution in a bottle was considered less proper and made it difficult to utilize the preparation in all connections (in a bus, at a party, etc.).

Comments

Dryness of the mouth causes a number of local symptoms in the oral cavity, the pharynx and the esophagus. The symptoms may cause disablement to the patient, physically as well as mentally. The aggressiveness and the frequency of the infectious diseases in the oral cavity will increase during xerostomia. The responses of the inquiries seem to indicate that the symptoms as to the pharynx and the esophagus as well as in connection with the upper respiratory tract are as troublesome as those of the oral cavity. Burning tongue seems to be the most pronounced symptom as to the mouth. The composition had a positive influence upon most of the symptoms in connection with xerostomia. The levels of the effect varied from one patient to another. It cannot be precluded that there was some placebo effect. However, all of the tested individuals had been troubled by their symptoms for relatively long periods of time. They had tested a number of preparations against xerostomia. Their abilities of evaluating the effect of a new preparation would therefore be relatively good. Moreover, the responses vary from one symptom to the other. If there were any placebo effects they would have been evenly distributed throughout the questions and the patients would have answered positively in a more consistent way if the placebo effects were large and decisive.

The results indicate that the composition had the best effect in patients having great troubles as the consequences of xerostomia.

RESULTS OF THE INQUIRES

TABLE 1

Duration of the xerostomia

| Patient: | Year |
|---|---|
| 1 | 20 |
| 2 | 5 |
| 3 | 5 |
| 4 | 3 |
| 5 | 5 |
| 6 | 7 |
| 7 | 6 |

TABLE 2

The effects on the general feeling of dryness of the mouth

| Patient: | Before | Effects |
|---|---|---|
| 1 | 3 | 3 |
| 2 | 5 | 2 |
| 3 | 5 | 2 |
| 4 | 3 | 3 |
| 5 | 5 | 5 |
| 6 | 4 | 1 |
| 7 | 5 | 4 |

EFFECTS ON BURNING OR INCONVENIENCES

TABLE 3

Cheeks

| Patient | Before | Effects |
|---|---|---|
| 1 | 4 | 5 |
| 2 | 1 | 4 |
| 3 | 1 | 1 |
| 4 | 2 | 0 |
| 5 | 2 | 5 |
| 6 | 1 | 1 |
| 7 | 2 | 3 |

TABLE 4

Tongue

| Patient | Before | Effects |
|---|---|---|
| 1 | 5 | 4 |
| 2 | 5 | 5 |
| 3 | 5 | 3 |
| 4 | 2 | 3 |
| 5 | 3 | 5 |
| 6 | 1 | 1 |
| 7 | 5 | 2 |

TABLE 5

Lips

| Patient | Before | Effects |
|---|---|---|
| 1 | 4 | 2 |
| 2 | 5 | 2 |
| 3 | 5 | 1 |
| 4 | 1 | 0 |
| 5 | 1 | 5 |
| 6 | 1 | 1 |
| 7 | 3 | 1 |

TABLE 6

Pharynx

| Patient | Before | Effects |
|---|---|---|
| 1 | 3 | 5 |
| 2 | 5 | 2 |
| 3 | 5 | 1 |
| 4 | 2 | 0 |
| 5 | 4 | 5 |

TABLE 6-continued

Pharynx

| Patient | Before | Effects |
|---|---|---|
| 6 | 1 | 1 |
| 7 | 3 | 3 |

TABLE 7

Oesophagus

| Patient | Before | Effects |
|---|---|---|
| 1 | 2 | 5 |
| 2 | 5 | 2 |
| 3 | 1 | 1 |
| 4 | 1 | 0 |
| 5 | 4 | 5 |
| 6 | 2 | 2 |
| 7 | 5 | 3 |

TABLE 8

Effects on the taste

| Patient | Before | Effects |
|---|---|---|
| 1 | 2 | 1 |
| 2 | 0 | 0 |
| 3 | 2 | 1 |
| 4 | 2 | 0 |
| 5 | 5 | 5 |
| 6 | 1 | 1 |
| 7 | 3 | 1 |

TABLE 9

Speech disorders

| Patient | Before | Effects |
|---|---|---|
| 1 | 3 | 3 |
| 2 | 5 | 2 |
| 3 | 5 | 2 |
| 4 | 3 | 3 |
| 5 | 5 | 5 |
| 6 | 4 | 1 |
| 7 | 5 | 4 |

TABLE 10

Swallowing problems

| Patient | Before | Effects |
|---|---|---|
| 1 | 3 | 5 |
| 2 | 3 | 4 |
| 3 | 4 | 3 |
| 4 | 2 | 2 |
| 5 | 3 | 4 |
| 6 | 3 | 1 |
| 7 | 5 | 2 |

TABLE 11

Chewings problems

| Patient | Before | Effects |
|---|---|---|
| 1 | 4 | 3 |
| 2 | 2 | 5 |
| 3 | 2 | 1 |
| 4 | 2 | 2 |
| 5 | 4 | 2 |
| 6 | 2 | 1 |
| 7 | 4 | 1 |

TABLE 12

Problems in connection with the brushing of teeth

| Patient | Before | Effects |
|---|---|---|
| 1 | 1 | 1 |
| 2 | 1 | 5 |

TABLE 12-continued

| Problems in connection with the brushing of teeth | | |
|---|---|---|
| Patient | Before | Effects |
| 3 | 1 | 1 |
| 4 | 1 | 2 |
| 5 | 3 | 2 |
| 6 | 1 | 1 |
| 7 | 1 | 1 |

TABLE 13

| Fissures in the mucosa | | |
|---|---|---|
| Patient | Before | Effects |
| 1 | 0 | 0 |
| 2 | 0 | 0 |
| 3 | 1 | 1 |
| 4 | 2 | 1 |
| 5 | 2 | 3 |
| 6 | 1 | 1 |
| 7 | 3 | 2 |

TABLE 14

| Time of the day when the symptoms were pronounced/ were alleviated to greatest extent | | | | | |
|---|---|---|---|---|---|
| Pat. | Morning | Middle o.t.day | Evening | Morning | Middle o.t.day | Evening |
| 1 | x | | | | x | |
| 2 | | x | | x | | |
| 3 | x | | | | | x |
| 4 | | x | | | | x |
| 5 | | x | | | x | |
| 6 | O | | | | O | |
| 7 | | x | | | x | |

TABLE 15

| Bad taste of the mouth | | |
|---|---|---|
| Patient | Before | Effects |
| 1 | 2 | 2 |
| 2 | 5 | 5 |
| 3 | 2 | 2 |
| 4 | 2 | 0 |
| 5 | 4 | 2 |
| 6 | 1 | 2 |
| 7 | 4 | 2 |

TABLE 16

| | Plaque index | | Gingival index | |
|---|---|---|---|---|
| Patient | Before | After | Before | After |
| 1. | 22 | 6 | 18 | 9 |
| 2. | 30 | 23 | 26 | 26 |
| 3. | 83 | 51 | 19 | 23 |
| 4. | 43 | 12 | 4 | 4 |
| 5. | 55 | 26 | 22 | 3 |
| 6. | 26 | 14 | 31 | 21 |
| 7. | 56 | 23 | 6 | 10 |
| Average Value | 45 | 23 | 18 | 14 |

We claim:

1. A composition for use as a saliva substitute, said composition comprising an effective amount of an aqueous solution of a water-soluble linseed polysaccharide having a viscosity within the range of 1-30 mPa.s, to be useful as a saliva substitute.

2. The composition as claimed in claim 1 wherein said aqueous solution has a viscosity within the range of 1-20 mPa.s.

3. The composition as claimed in claim 2 wherein said aqueous solution has a viscosity within the range of 2-10 mPa.s.

4. The composition as claimed in claim 1 wherein said linseed polysaccharide is prepared by extracting water-soluble linseed polysaccharides from linseed with water or an aqueous solution containing physiologically acceptable inorganic salts at a concentration of up to 3 mg per ml of water.

5. The composition as claimed in claim 4 wherein said physiologically acceptable inorganic salts are selected from the group consisting of sodium chloride and potassium bicarbonate.

6. The composition as claimed in claim 4 wherein the extracting is conducted at room temperature.

7. The composition as claimed in claim 1 wherein said composition further comprises a flavoring agent.

8. The composition as claimed in claim 1 wherein said composition further comprises a therapeutically active agent.

9. The composition as claimed in claim 8 wherein said therapeutically active agent is a member selected from the group consisting of an anti-fungal agent, an antiviral agent, an antibacterial agent, a corticosteroid, a lysozyme, and a fluorine compound of a combination thereof.

10. A method for substantially eliminating the symptoms of reduced salivary secretion in an individual in need thereof, said method comprising orally administering to an individual in need thereof an effective amount of an aqueous solution of a water soluble linseed polysaccharide having a viscosity within the range of 1-30 mPa.s, to prevent or treat reduced salivary secretion.

11. The method as claimed in claim 10 wherein said aqueous solution has a viscosity within the range of 1-20 mPa.s.

12. The method as claimed in claim 10 wherein said aqueous solution has a viscosity within the range of 2-10 mPa.s.

13. The method as claimed in claim 10 wherein said linseed polysaccharide is prepared by extracting water-soluble linseed polysaccharides from linseed with water or an aqueous solution containing physiologically acceptable inorganic salts at a concentration of up to 3 mg per ml of water.

14. The method of claim 13 wherein said physiologically acceptable inorganic salts are selected from the group consisting of sodium chloride and potassium bicarbonate.

15. The method as claimed in claim 13 wherein the extracting is conducted at room temperature.

16. The method as claimed in claim 10 wherein said aqueous solution further comprises a flavoring agent.

17. The method as claimed in claim 10 wherein said aqueous solution further comprises a therapeutically active agent.

18. The method as claimed in claim 17 wherein said therapeutically active agent is a member selected from the group consisting of an anti-fungal agent, an antiviral agent, an antibacterial agent, a corticosteroid, a lysozyme, and a fluorine compound or a combination thereof.

19. A process for the preparation of a saliva substitute, said process comprising (a) contacting linseed with water or an aqueous solution containing physiologically acceptable inorganic salts having a concentration up to 3 mg per ml of water to extract polysaccharides from said linseed and (b) separating the aqueous phase containing dissolved polysaccharides from the solid linseed residue.

20. The process as recited in claim 19, further comprising step (c) drying the aqueous phase to obtain a dry product which can later be reconstituted as a saliva substitute.

21. The process as recited in claim 19 wherein said physiologically acceptable inorganic salts are selected from the group consisting of sodium chloride and potassium bicarbonate.

22. The process as claimed in claim 19 wherein the viscosity is adjusted to 1-30 mPa.s.

23. The process as claimed in claim 19 wherein the viscosity is adjusted to 1-20 mPa.s.

24. The process as claimed in claim 23 wherein the viscosity is adjusted to 2-10 mPa.s.

25. A process for the preparation of a saliva substitute, said process comprising (a) contacting linseed with water or an aqueous solution containing physiologically acceptable inorganic salts having a concentration up to 3 mg per ml of water to extract polysaccharides from linseed, (b) separating the aqueous phase containing dissolved polysaccharides from the solid linseed residue and (c) adjusting the concentration of said aqueous phase to 1-30 mPa.s.

* * * * *